United States Patent [19]
Clarén

[11] Patent Number: 4,787,882
[45] Date of Patent: Nov. 29, 1988

[54] TWO STAGE VENOUS RETURN CATHETER
[75] Inventor: Jan S. Clarén, Lund, Sweden
[73] Assignee: Gambro AB, Sweden
[21] Appl. No.: 945,848
[22] Filed: Dec. 23, 1986
[30] Foreign Application Priority Data
   Jan. 16, 1986 [SE] Sweden .................. 8600188
[51] Int. Cl.⁴ .................. A61M 1/03; A61M 25/00
[52] U.S. Cl. .................. 604/4; 604/249; 604/256; 604/264
[58] Field of Search .................. 604/4, 27, 43, 247, 604/256, 264, 93, 249, 280–284

[56] References Cited
U.S. PATENT DOCUMENTS

| | | | |
|---|---|---|---|
| 4,129,129 | 12/1978 | Amrine | 604/43 |
| 4,184,497 | 1/1980 | Kolff et al. | 604/27 |
| 4,204,328 | 5/1980 | Kutner | 604/256 |
| 4,639,252 | 1/1987 | Kelly et al. | 604/4 |
| 4,643,712 | 2/1987 | Kulik et al. | 604/264 |
| 4,666,426 | 5/1987 | Aigner | 604/43 |

Primary Examiner—Barry S. Richman
Assistant Examiner—T. J. Wallen
Attorney, Agent, or Firm—Lerner, David, Littenberg, Krumholz & Mentlik

[57] ABSTRACT

Catheters are disclosed which are adapted for insertion into the heart and which include at least one inlet opening at the front end thereof, at least one outlet opening at the other end thereof, and at least one intermediate opening therebetween, and which include a cylindrical sleeve for opening and closing the intermediate opening so that it can be selectively opened and closed thereby. These catheters are employed most particularly for the withdrawal of blood from both the inferior vena cava and from the right auricle and/or from the superior vena cava of the heart.

18 Claims, 4 Drawing Sheets

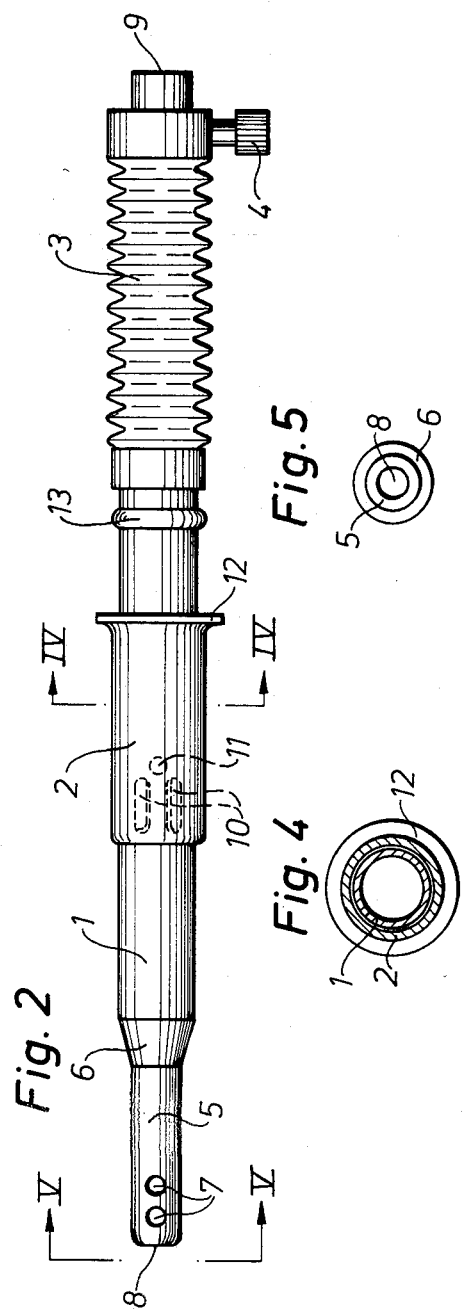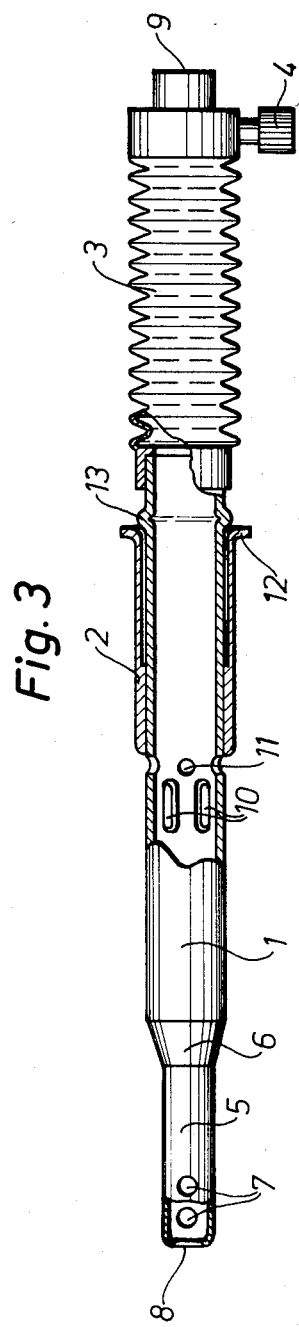

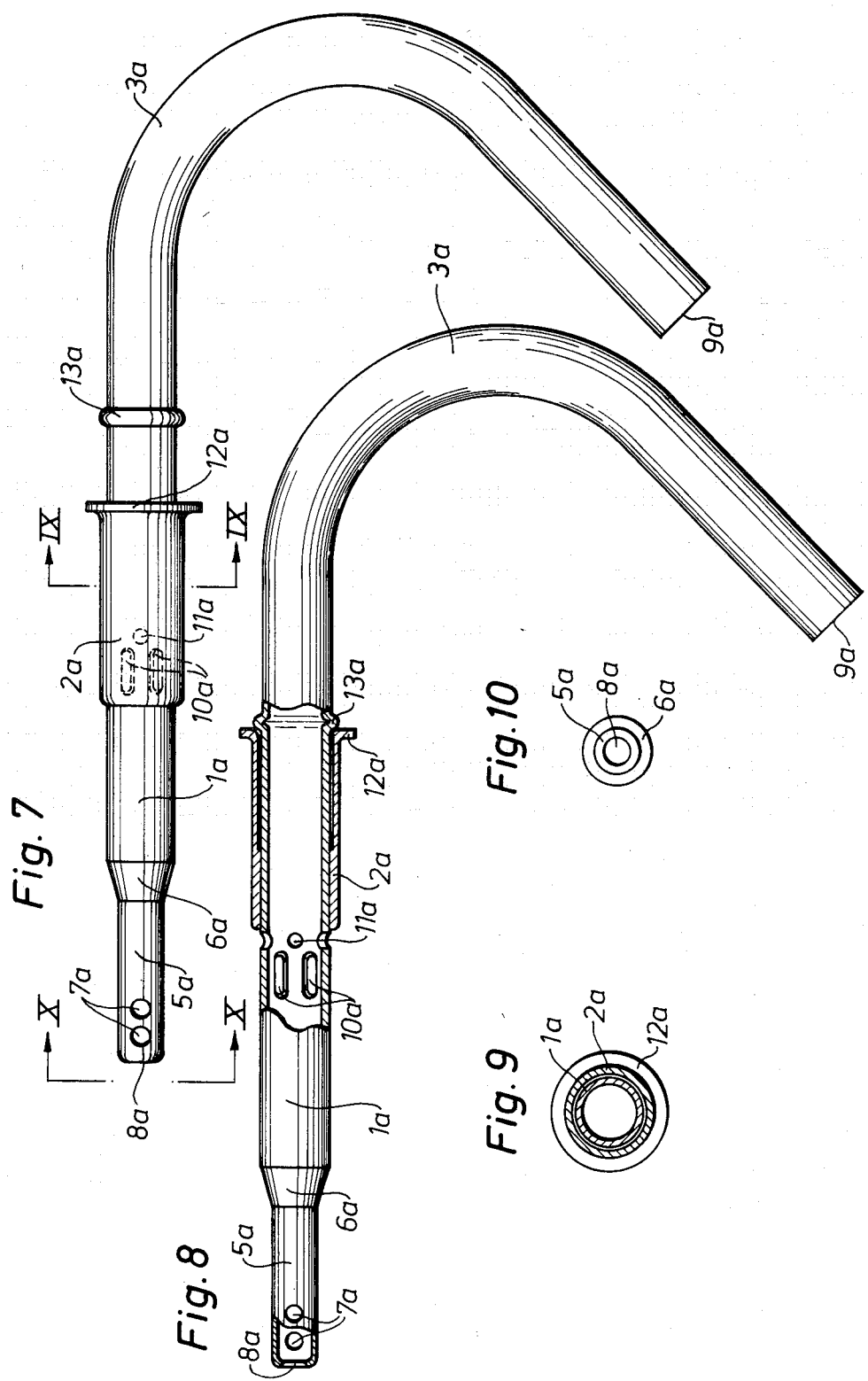

4,787,882

TWO STAGE VENOUS RETURN CATHETER

FIELD OF THE INVENTION

The present invention relates to catheters. More particularly, the present invention relates to cardiac catheters including at least one inlet opening at one end, and at least one outlet opening at its other end, and including an intermediate opening therebetween. The present invention is more particularly directed to cardiac catheters to be used for the withdrawal of blood from the inferior vena cava on the one hand and from the right auricle of the heart and/or the superior vena cava on the other hand.

BACKGROUND OF THE INVENTION

A known cardiac catheter is disclosed in Amrine, U.S. Pat. No. 4,129,129. This catheter includes two sets of openings, namely those at the rounded nose portion of the catheter which is intended to enter the inferior vena cava, and those at the juncture between the differing diameter portions of this catheter, which are intended to be placed in the right atrium. The use of such a catheter, however, has been relatively troublesome for several reasons, including the fact that a part of the catheter must be removed in order to achieve the desired flow through the different openings. Furthermore, this overall design is somewhat difficult to use because it is relatively large and because it is also essentially stiff.

Various other medical suction devices are also known, such as that shown in U.S. Pat. No. 3,395,705 to Hamilton, which includes flow regulating means for use in a suction line between a medical catheter and a suction pump for the purpose of varying the amounts of suction being applied to a catheter. Similar types of suction devices are also shown in Swedish Patent Publication No. 337,888; Swedish Patent Publication No. 429,005; Swedish Patent Application No. 84.00747-5; and U.S. Pat. No. 3,834,388 to Sauer. In addition, a heart catheter intended to be used in an entirely different manner from those of the present invention and also as compared to the above-noted Amrine patent are shown in U.S. Pat. No. 2,935,068 to Donaldson.

SUMMARY OF THE INVENTION

In accordance with the present invention, improved cardiac catheter devices of the above-described type have now been discovered by the provision of a cardiac catheter which includes an elongated tubular catheter body including a first end and a second end, the first end being adapted for insertion into the heart and including at least one inlet opening for admitting fluid such as blood into the catheter body, and a second end comprising an outlet for that fluid, the catheter body also including an intermediate portion between the first and second ends which includes at least one intermediate opening for admitting additional fluid into the catheter body, an intermediate opening closure means for closing the at least one intermediate opening so that it can be selectively opened for the selective admission of additional fluid into the catheter therethrough. Therefore, in accordance with this invention, the intermediate opening or openings arranged on an essentially cylindrical portion of the catheter body which preferably includes a slidable arrangement which is displaceable preferably axially, thereon for opening and closing these intermediate openings. Alternatively said arrangement may be bendable. By employing such a device, particularly including such a sliding mechanism for opening and closing, it is now possible for the device to be readily accessible to the user, and it therefore becomes unnecessary to remove any part from the catheter in order to maintain the intermediate openings in the open position.

In accordance with one embodiment of the cardiac catheter of the present invention, the intermediate portion of the catheter body is cylindrical, and the intermediate opening closure means comprises a slide means which is slidable along the intermediate portion of the catheter body to selectively open and close the intermediate openings. The slide means thus preferably comprises a cylindrical sleeve having the same cross-sectional shape as the cylindrical shape of the catheter body, i.e., preferably circular. Furthermore, in this manner it can be relatively easily insured that the slidable member cannot be detached from the remainder of the catheter body.

In accordance with another embodiment of the cardiac catheter of the present invention, the first end of the catheter body includes a plurality of inlet openings. Preferably the intermediate portion of the catheter body also includes a plurality of intermediate openings, and most preferably these include at least one elongated intermediate opening and at least one circular intermediate opening.

In accordance with a preferred embodiment of the cardiac catheter of the present invention, the cylindrical sleeve member includes a raidally projecting flange member so that the cylindrical sleeve can be gripped thereby. Furthermore, it is preferred that the intermediate opening closure means be slidable between the first position in which the at least one intermediate opening is closed and a second position in which the opening is uncovered and in which the catheter body includes a stop means for defining the limit of movement of the intermediate opening and closure means at the second position. This further facilitates handling of the slidable sleeve member or the like.

In accordance with another embodiment of the cardiac catheter of the present invention, the first end of the catheter body includes a narrow cylindrical portion having a first diameter, and the intermediate portion of the catheter body has a second diameter, with the first diameter being less than the second diameter. The narrow cylindrical portion having the smaller diameter is preferably formed by heating and compressing or by shrinking the first end of the previously uniformly thick catheter body.

In accordance with another embodiment of the cardiac catheter of the present invention, the stop means comprises a shaped portion of the intermediate portion of the catheter body, which is preferably produced by forming or upsetting the heated portion of the catheter body itself into the shape of a rounded radially projecting flange.

In accordance with a preferred embodiment of the cardiac catheter of the present invention, the second end of the catheter body includes angled extension means facing in a direction which forms an angle with respect to the longitudinal axis of the catheter body to facilitate handling of same. In another embodiment the second end of the catheter body includes bendable extension means for permitting the second end of the catheter body to be bent in a direction which forms an angle with respect to the longitudinal axis of the catheter body, and preferably the bendable extension means comprises bellows means.

The cardiac catheters of the present invention are normally connected to a flexible tube system filled with priming fluid. For this reason the cardiac catheters of the present invention are preferably provided with an evacuating arrangement for the withdrawal of any air which may accumulate between the blood and the priming fluid introduced therein. The evacuating means preferably comprises a check valve, but may also comprise an injection port so that the port can be coupled to an external pump. When the injection port comprises an elastic membrane, it can be pierced by an external pump, such as a syringe. In the case where a check valve is used, it is preferably employed in connection with the use of a catheter including the abovementioned bellows means, which can itself then be used as a pump for forcing out accumulated air through such a check valve.

The catheter of the present invention is particularly useful as a cardiac catheter for the withdrawal of blood both from the "inferior vena cava" and from the right auricle of the heart and/or the "superior vena cava." The slidable sleeve means is thus used in such a case for opening and closing of the intermediate opening and/or openings as the catheter is introduced into and/or taken out of the heart, respectively.

BRIEF DESCRIPTION OF THE DRAWINGS

The following detailed description of the cardiac catheters of the present invention may be more fully understood with reference to the enclosed drawings in which:

FIG. 2 is a side, elevational view of the cardiac catheter shown in FIG. 1;

FIG. 3 is a side, partially sectional view of the cardiac catheter shown in FIG. 2;

FIG. 4 is a front, cross-sectional view of the cardiac catheter of FIG. 2 taken along lines IV—IV thereof;

FIG. 5 is a front, elevational view of the cardiac catheter shown in FIG. 2 taken along lines V—V thereof;

FIG. 7 is a side, elevational view of the cardiac catheter shown in FIG. 6;

FIG. 8 is a side, partially sectional view of the cardiac catheter shown in FIG. 7;

FIG. 9 is a front, sectional view of the cardiac catheter shown in FIG. 7, taken along lines IX—IX thereof; and FIG. 10 is a front view of the cardiac catheter shown in FIG. 7 taken along lines X—X thereof.

DETAILED DESCRIPTION

Figure 1:
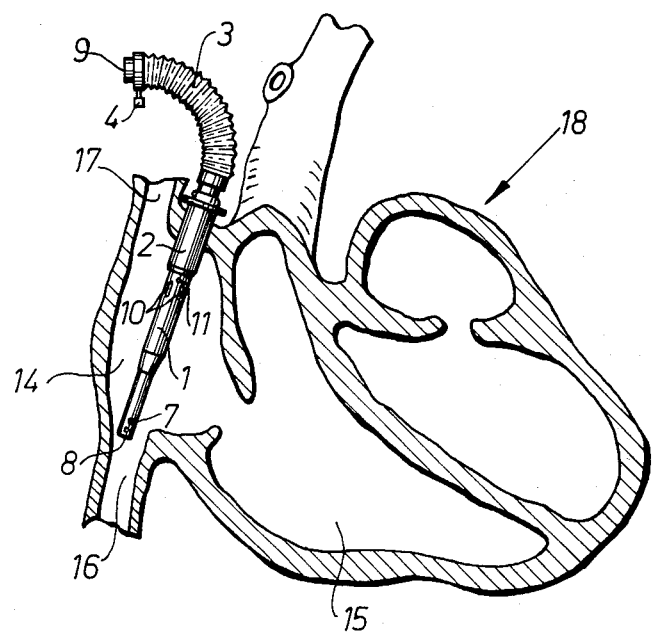
FIG. 1 is an elevational, side view of an embodiment of the cardiac catheter of the present invention shown inserted into a heart.

Referring to the figures, in which like numerals refer to the like portions thereof, the embodiment of the cardiac catheters of the present invention shown in FIGS. 1–5 includes a main portion 1 with a slide 2 displaceable thereon, and a bellows-like portion 3 connected thereto, and which is combined with means for 15, the "inferior vena cava" 16, and the "superior vena cava" 17. In the position shown, the catheter is thus used for withdrawing blood from the "inferior vena cava" 16, and the right auricle 14. The catheter is appropriately brought into such a working position in a straight, substantially vertical position, with the openings 10 and 11 initially covered by the slide 2. In this manner, blood entering through the inlet openings 7 and 8 cannot flow through intermediate openings 10 and 11 before these have pushed through the intermediate wall of the heart. During this phase of operation the blood will thus flow upwardly into the catheter to a certain level, but normally not up to outlet opening 9. Subsequently, the remaining space within the catheter can be filled, either wholly or partly, with priming fluid, i.e., a fluid which is miscible with the blood, before the catheter is connected to a flexible tube system which is filled with similar priming fluid, and which may be connected, for example, to an oxygenator. Any air which may be entrapped within the catheter during this process can then be removed with the assistance of evacuating arrangement 4. This may, for example, comprise a check valve through which such entrained air can be pumped out, such as with the help of the bellows-like portion 3, which can thus be used in the manner of a pump. Alternatively, the evacuating arrangement 4 can comprise a so-called injection port, which can comprise an elastic membrane, plug or the like, and which is adapted so that it can be pierced by an injection syringe or the like, by means of which entrapped air can be extracted. Numeral 18 in FIG. 1 generally designates the heart as a whole. evacuating 4. The front portion 5 of the main portion 1 has a smaller diameter than the main portion 1, and is connected to the main portion via a conical intermediate section 6. In the front portion 5 there are provided a number of inlet openings, 7 and 8. At the opposite end of the catheter there is provided an outlet opening 9, which is intended to be connected, for example, to a flexible tube system (not shown) for ultimate connection to an oxygenator or the like.

Between the inlet openings 7 and 8 and the outlet opening 9 there are provided intermediate openings 10 and 11, respectively, on the main portion 1. Intermediate openings 10 are oblong, whereas intermediate openings 11 are circular. These openings 10 and 11 can be covered by the displaceable slide 2, whose displacement is facilitated by means of a gripping flange 12. As shown in FIG. 3, a fully opened position is produced by the gripping flange being guided towards a stop flange 13, which is formed by upsetting or molding of the actual main portion 1. At the same time, the gripping flange marks the maximum depth of insertion of the catheter into the heart.

The bellows-like portion 3 can be attached to the main portion 1 by means of glueing or welding, for example. Alternatively, these two parts may be comprised of a single piece, by means of a technique known in itself.

Figure 6:
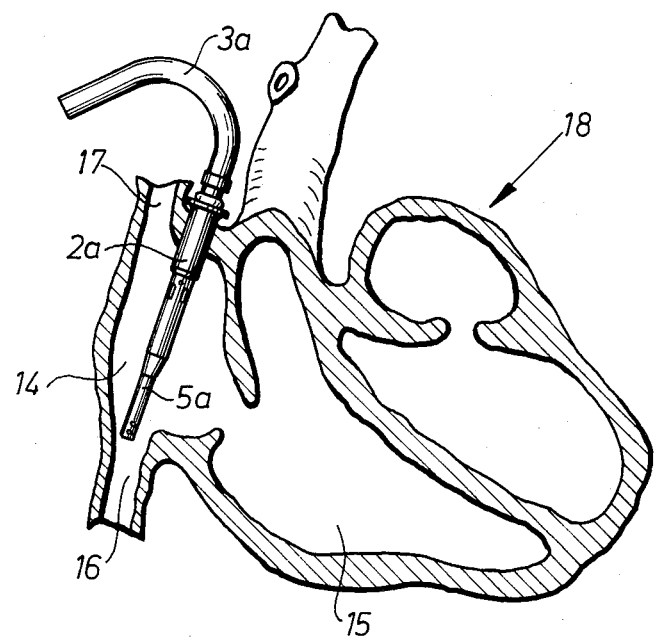
FIG. 6 is a side, elevational view of another embodiment of the cardiac catheter of the present invention shown in conjunction with a heart.

The method by which such catheters are intended to actually be used in practice is described in detail in the abovementioned U.S. Pat. No. 4,129,129, and that portion thereof as incorporated herein by reference thereto. The means of application of this device is illustrated, however, in FIG. 1, where there is drawn the right auricle 14, the right ventricle Turning to the embodiment shown in FIGS. 6–10, a slightly simplified embodiment of the present invention is shown therein. The overall design and function of the catheter is substantially the same as for the catheter described above, however. For this reason, the same reference numerals have been used for corresponding parts, but with the additional letter a. Thus 1a designates the main portion of the catheter, and 2a its slide. The bellows-like portion 3, however has been substituted for in this case by a plain portion 3a, which may be either rigid or bendable into the position shown. This catheter can, of course, also be provided with an evacuating arrangement, even though none is shown in these drawings. Like the catheter shown in FIGS. 1–5, this catheter can also be used in essentially the same manner as the catheter described in U.S. Pat. No. 4,129,129, but without the disadvantages of the same.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

I claim:

1. A cardiac catheter comprising a tubular catheter body including a first end and a second end, said first end of said catheter body being adapted for insertion into heart and including at least one inlet opening for admitting fluid into said catheter body, and said second end of said catheter body comprising an outlet for said fluid, said catheter body including an intermediate portion between first end and said second end, said intermediate portion of said catheter body including at least one intermediate opening for admitting additional fluid into said catheter body, and intermediate opening closure means movable between a first position wherein said intermediate opening closure means leaves both said at least one inlet opening and said at least one intermediate opening open for the admission of fluid into said catheter body therethrough, and a second position wherein said intermediate opening closure means leaves said at least one inlet opening free for the admission of fluid into said catheter body therethrough while closing said at least one intermediate opening, said catheter body including a longitudinal axis and said second end of said catheter body including bendable extension means comprising bellow means for permitting said second end of said catheter body to be bent in a direction which forms an angle with respect to said longitudinal axis of said catheter body.

2. The cardiac catheter of claim 1 including evacuating means for withdrawing any air contained within said catheter body therefrom.

3. The cardiac catheter of claim 2 wherein said evacuating means comprises check valve means.

4. A cardiac catheter comprising a tubular catheter body including a first end and a second end, said first end of said catheter body being adapted for insertion into heart and including at least one inlet opening for admitting fluid into said catheter body, and said second end of said catheter body comprising an outlet for said fluid, said catheter body including an intermediate portion between first end and said second end, said intermediate portion of said catheter body including at least one intermediate opening for admitting additional fluid into said catheter body, and intermediate opening closure means movable between a first position wherein said intermediate opening closure means leaves both said at least one inlet opening and said at least one intermediate opening open for the admission of fluid into said catheter body therethrough, and a second position wherein said intermediate opening closure means leaves said at least one inlet opening free for the admission of fluid into said catheter body therethrough while closing said at least one intermediate opening, and evacuating means for withdrawing any air contained within said catheter body, said evacuating means comprising an injection port having penetrable cover means, whereby said injection port can be coupled to external pump means.

5. The cardiac catheter of claim 1 or 4 wherein said intermediate portion of said catheter body is cylindrical, and wherein said intermediate opening closure means comprises a slide means slidable upon said intermediate portion of said catheter body for selectively opening and closing said at least one intermediate opening.

6. The cardiac catheter of claim 5 wherein said slide means comprises a cylindrical sleeve member.

7. The cardiac catheter of claim 3 wherein said cylindrical sleeve member includes a radially projecting flange member whereby said cylindrical sleeve member can be gripped thereby.

8. The cardiac catheter of claim 1 or 4 wherein said first end of said catheter body includes a plurality of inlet openings.

9. The cardiac catheter of claim 1 or 4 wherein said intermediate portion of said catheter body includes a plurality of intermediate openings.

10. The cardiac catheter of claim 9 wherein said plurality of intermediate openings comprises at least one intermediate opening having a predetermined length and width, said predetermined length being substantially greater than said predetermined width and at least one circular intermediate opening.

11. The cardiac catheter of claim 1 or 4 wherein said first end of said catheter body includes a cylindrical portion having a first diameter, and wherein said intermediate portion of said catheter body has a second diameter, and wherein said first diameter is less than said second diameter.

12. The cardiac catheter of claim 4 wherein said catheter body includes a longitudinal axis and said second end of said catheter body includes extension means including a curved surface, whereby said second end of said catheter body faces in a direction away from said longitudinal axis of said catheter body.

13. The cardiac catheter of claim 4 wherein said catheter body includes a longitudinal axis and said second end of said catheter body includes bendable extension means for permitting said second end of said catheter body to be bent in a direction which forms an angle with respect to said longitudinal axis of said catheter body.

14. The cardiac catheter of claim 13 wherein said bendable extension means comprises bellows means.

15. The cardiac catheter of claim 4 wherein siad injection port comprises an elastic membrane adapted to be pierced by an external pump comprising a syringe means.

16. The cardiac catheter of claim 1 or 4, wherein said catheter body includes stop means for defining the limit of movement of said intermediate opening closure means at said second position.

17. The cardiac catheter of claim 16 wherein said stop means comprises a shaped portion of said intermediate portion of said catheter body.

18. The cardiac catheter of claim 4, wherein said evacuating means comprises check valve means.

* * * * *

UNITED STATES PATENT AND TRADEMARK OFFICE
CERTIFICATE OF CORRECTION

PATENT NO. :      4,787,882                              Page 1 of 2

DATED       :     November 29, 1988

INVENTOR(S) :     Jan S. Claren

It is certified that error appears in the above-identified patent and that said Letters Patent is hereby corrected as shown below:

Column 3, after line 65, insert:

--evacuating 4. The front portion 5 of the main portion 1 has a smaller diameter than the main portion 1, and is connected to the main portion via a conical intermediate section 6. In the front portion 5 there are provided a number of inlet openings, 7 and 8. At the opposite end of the catheter there is provided an outlet opening 9, which is intended to be connected, for example, to a flexible tube system (not shown) for ultimate connection to an oxygenator or the like.

Between the inlet openings 7 and 8 and the outlet opening 9 there are provided intermediate openings 10 and 11, respectively, on the main portion 1. Intermedite openings 10 are oblong, whereas intermediate openings 11 are circular. These openings 10 and 11 can be covered by the displaceable slide 2, whose displacement is facilitated by means of a gripping flange 12. As shown in FIG. 3, a fully opened position is produced by the gripping flange being guided towards a stop flange 13, which is formed by upsetting or molding of the actual main portion 1. At the same time, the gripping flange marks the maximum depth of insertion of the catheter into the heart.

The bellows-like portion 3 can be attached to the main portion 1 by means of glueing or welding, for example. Alternatively, these two parts may be comprised of a single piece, by means of a technique known in itself.

The method by which such catheters are intended to actually be used in practice is described in detail in the above-mentioned U.S. Pat. No. 4,129,129, and that portion thereof as incorporated herein by reference thereto. The means of application of this device is illustrated, however, in FIG. 1 where there is drawn the right auricle 14, the right ventricle--

UNITED STATES PATENT AND TRADEMARK OFFICE
CERTIFICATE OF CORRECTION

PATENT NO. : 4,787,882
DATED : November 29, 1988
INVENTOR(S) : Jan S. Claren

Page 2 of 2

It is certified that error appears in the above-identified patent and that said Letters Patent is hereby corrected as shown below:

Column 4, line 29, delete "evacuating 4. The front portion 5".

Column 4, delete lines 30 through 62 in their entirety.

Column 6, line 17, "claim 3" should read --claim 6--.

Column 6, line 55, "siad" should read --said--.

Signed and Sealed this

Fourth Day of July, 1989

Attest:

DONALD J. QUIGG

*Attesting Officer*

Commissioner of Patents and Trademarks